(12) United States Patent
Wu

(10) Patent No.: US 9,560,447 B2
(45) Date of Patent: Jan. 31, 2017

(54) BLIND EXTRACTION OF TARGET SIGNALS

(71) Applicant: Wayne State University, Detroit, MI (US)

(72) Inventor: Sean F Wu, Troy, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 14/356,771

(22) PCT Filed: Nov. 7, 2012

(86) PCT No.: PCT/US2012/063769
§ 371 (c)(1),
(2) Date: May 7, 2014

(87) PCT Pub. No.: WO2013/070643
PCT Pub. Date: May 16, 2013

(65) Prior Publication Data
US 2014/0301555 A1    Oct. 9, 2014

Related U.S. Application Data

(60) Provisional application No. 61/556,516, filed on Nov. 7, 2011.

(51) Int. Cl.
*H04R 29/00* (2006.01)
*H04R 3/04* (2006.01)
(Continued)

(52) U.S. Cl.
CPC ............... *H04R 3/04* (2013.01); *A61B 5/726*
(2013.01); *A61B 5/7278* (2013.01); *G06K 9/00516* (2013.01); *A61B 5/08* (2013.01)

(58) Field of Classification Search
CPC ......... H04R 3/04; A61B 5/726; A61B 5/7278; A61B 5/08; G06K 9/00516
See application file for complete search history.

(56) References Cited

U.S. PATENT DOCUMENTS

2004/0135872 A1    7/2004  Burdenko
2004/0138572 A1*   7/2004  Thiagarajan ................. 600/508
(Continued)

OTHER PUBLICATIONS

International Search Report mailed Jan. 31, 2013.

*Primary Examiner* — Andrew L Sniezek
(74) *Attorney, Agent, or Firm* — Carlson, Gaskey & Olds, P.C.

(57) ABSTRACT

A system and method allow for extracting target signals from the overall measurement data without knowing how and where these data are collected, the locations and characteristics of target sources as well as those of random background noise sources. In essence, it uses an innovative and advanced signal processing technique to reveal certain critical information from a mixture of data that is hard to obtain otherwise. In particular, it allows for denoising the measured data that have been contaminated by various interfering and background noise, making it possible to extract certain target information that may be otherwise difficult to observe. The only assumption made in this method is that the target signal is incoherent with respect to all interfering signals and background noise. The more information about a target signal is available, the more complete the extracted signal becomes.

10 Claims, 3 Drawing Sheets

(51) Int. Cl.
*A61B 5/00* (2006.01)
*G06K 9/00* (2006.01)
*A61B 5/08* (2006.01)

(56) References Cited

U.S. PATENT DOCUMENTS

| 2008/0183466 A1* | 7/2008 | Nongpiur et al. ............ 704/226 |
| 2009/0324034 A1 | 12/2009 | Watson et al. |
| 2010/0307251 A1* | 12/2010 | Welle et al. .................... 73/627 |
| 2011/0038537 A1 | 2/2011 | Rising |
| 2012/0123689 A1 | 5/2012 | Addison et al. |

* cited by examiner

BLIND EXTRACTION OF TARGET SIGNALS

BACKGROUND

In practice, almost all signals are contaminated to certain degree by interfering signals and background noise. Since the test environment is usually non-ideal, contamination in data collection is unavoidable. Meanwhile, the test environment is typically arbitrary, and interfering signals and background noise are unknown a priori. As such, it is extremely challenging to extract target information from a mixture of data that include some unknown number of interfering signals and random background noise.

Common signal processing technologies such as the Fourier transform and short-time Fourier transform do not work, because they cannot handle the signals that are varying in time and frequency in an arbitrary manner. The wavelet transform allows for converting an arbitrary time signal into a form that either makes certain features of the original signal more amenable to study or enables the original data set to be described more succinctly. However, the standard discrete wavelet transform cannot be used directly to extract desired information from the measured data. This is because the discrete wavelet transform decomposes an arbitrary time signal into various scales, and displays their corresponding behaviors in the time domain at these scales. Such a treatment makes it difficult to analyze the behaviors of various components and features of the measured data, which is critical for extracting the desired information in practice.

SUMMARY

A method and system disclosed herein extracts target information from a mixture of time domain signals measured by any hardware without knowing how and where these signals are collected, and what the test environment and condition may be. Therefore, it can be a completely blind extraction of target signal. It is emphasized, however, that the quality of extracted information may be significantly improved if specific characteristics of the target signal are incorporated in the calculation. In other words, the more information regarding the target signal is utilized, the higher the fidelity of the extracted information becomes.

This method is built on the standard wavelet transform but goes one step further by converting the decomposed components at all scales into the $1^{st}$ scale in the time domain to facilitate an analysis of the individual features and characteristics contained in the measured data. Such an approach enables one to identify the desired information from the measured data that may have been contaminated by various unknown interfering signals and random background noise.

This approach is applicable to any time domain signals, regardless of their physical nature. For example, it can be used to analyze acoustic pressures, vibrations, fluid flows, temperature fluctuations, just to name a few. There are no restrictions on the minimum number of channels (it even works for a single channel data acquisition system), no restrictions on where and how input data should be collected, and no requirements on prior knowledge of the locations of target, interfering sources and background noise. The only assumption made in this approach is that the target information is incoherent with the interfering signals and random background noise. For example, the signal from the exhaust of an automobile engine has its own characteristics that are different from and incoherent with those from engine cylinders or manifolds, as well as those from random background noise. Therefore, by using the proposed method, we may be able to extract the unique feature of engine exhaust signal from the overall measured data. Similarly, we can use this new technology to collect intelligence such as extracting the suspect's voice from directly measured data that have been contaminated by random background noise, conducting in-line or end-of-line products QC testing on a noisy factory floor, etc.

This approach permits extracting target signals from overall measurement data without any prior knowledge of source locations and/or characteristics of the target sources. In essence it is a hybrid approach for conducting signal processing and analysis to reveal some critical information of specific target sources that may not be obtained otherwise. In particular, it is suitable for de-noising the measured signals that are contaminated by various interfering and background noise, making it possible to observe target signals that are otherwise difficult to observe. Because the algorithms are of generality, this method is suitable for any type of signals, for example, acoustics, vibrations, neural activities inside the brain auditory, etc. As such, its potential application can be found in intelligence gathering, listening to target suspect's conversations taking place in a noisy environment, in-line/end-of-line product quality control (QC) testing, on-site product quality evaluation on a manufacturing floor, clinical diagnosis of tinnitus-related neural activities in the auditory brain structures including the dorsal cochlear nucleus, inferior colliculus, and auditory cortex, which have been implicated in the etiology of tinnitus, and diagnosis of other neurological disorders, for example, central auditory processing disorders, Parkinson's Disease, Alzheimer's disease, etc.

DETAILED DESCRIPTION OF A PREFERRED EMBODIMENT

Figure 1:
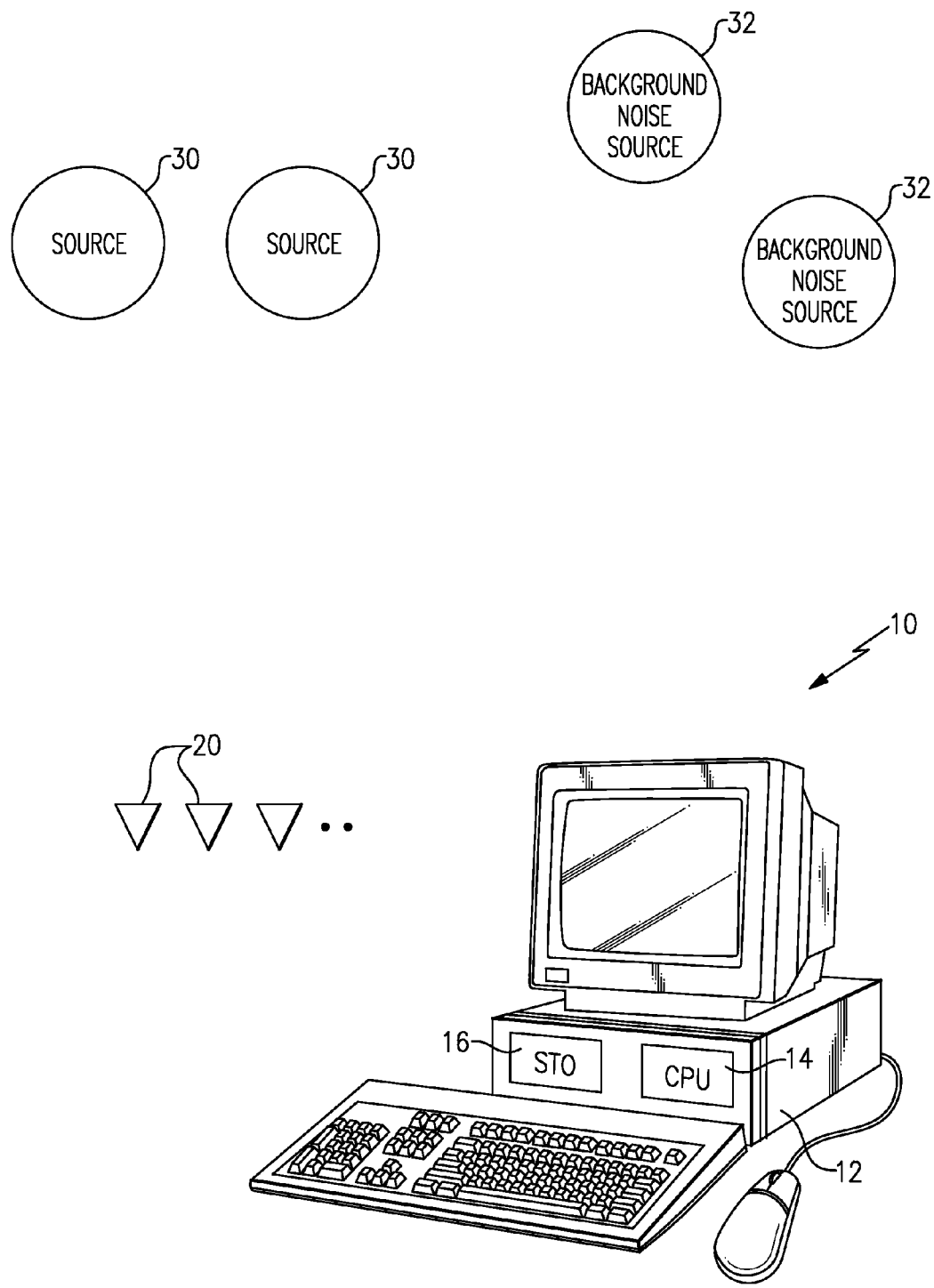
FIG. 1 is a schematic of the target information extraction system according to one embodiment.

A target information extraction system 10 according to the present invention includes a computer 12 having a processor 14 and storage 16 including memory and mass storage, such as magnetic, electronic and/or optical storage. One or more transducers 20, such as microphones, probes and other sensors, may be used to measure sound pressure (or other physical signals) and send signals to the computer 12 indicating the capture of sound pressure (or other physical signals) at the location of the transducers 20.

The target information extraction system 10 of the present invention uses an algorithm described below to extract information from one or more target sources 30. The algorithm is stored in storage 16 and executed by the processor 14 in the computer 12. The computer 12 is programmed to perform the outlined steps using the algorithms described herein and any necessary functions. The location, number and nature of the sources 30 and background noise sources 32 may be unknown. The transducers 20 or sensors are suitable for the type of target signals being measured, such as microphones, vibration sensors, etc.

Figure 2:
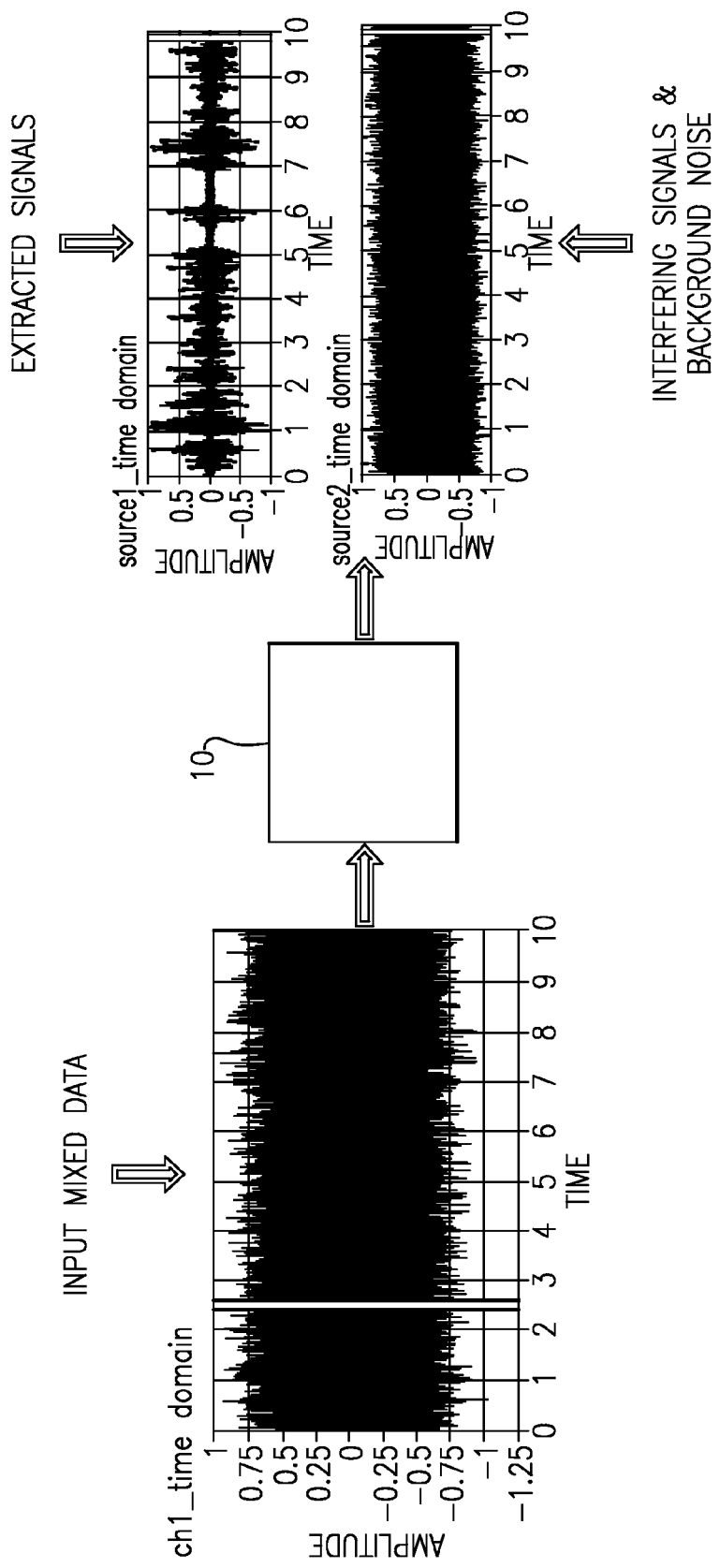
FIG. 2 is a schematic of this new process to extract some target information from measured data.

FIG. 2 shows the schematic of the system 10 to extract target information from a mixture of data collected in a non-ideal environment. The input to this new process is directly measured data that may have been contaminated by interfering signals and random background noise. The output is the target information. This algorithm can process the time-domain signals collected by any hardware and/or data acquisition system. It has no special requirement for specific hardware required for this algorithm to work.

In general, the coherent structure of a mixture of data can be extracted and written as follows by using the D4 Daubechies wavelets as follows $$\{x\}_{N\times 1} = 2^{-1/2} [C]_{N\times N}^T \{\hat{W}^{(1)}\}_{N\times 1}, \qquad (1)$$

where $\{x\}_{N\times 1}$ represents a column vector containing the extracted data, $[C]_{N\times N}^T$ indicates the transpose of the square matrix $[C]_{N\times N}$ that contains the scaling coefficients, and $\hat{W}^{(1)}$ is the wavelet vector at scale m=1 after threshold. Note that one can select any threshold. In this case, we choose the universal threshold $$\lambda_U = \sqrt{2\ln N}\hat{\sigma}, \qquad (2)$$

where $(2 \ln N)^{1/2}$ is the expected maximum value of a white noise sequence of length N, namely, there are N data points in the sequence, and $\hat{\sigma}$ is a robust estimate of the standard deviation of the noise in the input data under consideration. Typically, $\hat{\sigma}$ is taken at the median of absolute deviation (MAD) of the wavelet coefficients at the smallest scale m=1, divided by 0.6745 to calibrate with the standard deviation of a Gaussian distribution, where $\hat{\sigma}=0.6745\times$ median[$|T_{1,i}-$median$(T_{1,i})|$], $T_{1,i}$ represents the wavelet coefficients at scale m=1.

In the universal threshold, all wavelet coefficients are compared with $\lambda_U$. The coefficients that are larger than this threshold are deemed to correspond to the coherent parts of target information and kept intact; and those less the threshold $\lambda_U$ are deemed incoherent or noisy parts of the input data and are eliminated.

$$\hat{W}_i^{(1)} = \begin{cases} 0 & |\hat{W}_i^{(1)}| < \lambda_U \\ \hat{W}_i^{(1)} & |\hat{W}_i^{(1)}| \geq \lambda_U \end{cases}, \qquad (3)$$

Note that the elements of the square matrix $[C]_{N\times N}$ in Eq. (1) change with the choice of extensions of the input data, depending on the type of Daubechies wavelets are used. When a simple convolution is used to extend the input data, the square matrix $[C]_{N\times N}$ is expressible as $$[C]_{N\times N} = \begin{bmatrix} c_0 & c_1 & c_2 & c_3 & 0 & 0 & \ldots & \ldots & 0 & 0 \\ c_3 & -c_2 & c_1 & -c_0 & 0 & 0 & \ldots & \ldots & 0 & 0 \\ 0 & 0 & c_0 & c_1 & c_2 & c_3 & 0 & \ldots & 0 & 0 \\ 0 & 0 & c_3 & -c_2 & c_1 & -c_0 & 0 & \ldots & 0 & 0 \\ \vdots & \vdots & \vdots & \vdots & \vdots & \vdots & \vdots & \vdots & \vdots & \vdots \\ \vdots & \vdots & \vdots & \vdots & \vdots & \vdots & \vdots & \vdots & \vdots & \vdots \\ 0 & 0 & 0 & 0 & \ldots & \vdots & \vdots & \vdots & \vdots & \vdots \\ c_2 & c_3 & 0 & 0 & \ldots & \ldots & 0 & 0 & c_0 & c_1 \\ c_1 & -c_0 & 0 & 0 & \ldots & \ldots & 0 & 0 & c_3 & -c_2 \end{bmatrix}_{N\times N} \qquad (4)$$

Because of the constraint conditions for the D4 Daubechies wavelets, we have $$c_0^2 + c_1^2 + c_2^2 + c_3^2 = 3 \text{ and } c_0 c_2 + c_1 c_3 = 0. \qquad (5)$$

Therefore, the product of $[C]_{N\times N}^T$ and $[C]_{N\times N}$ is a diagonal and unitary matrix multiplied by 2.

$$[C]_{N\times N}^T [C]_{N\times N} = 2[I]_{N\times N}, \qquad (6)$$

where $[I]_{N\times N}$ indicates an identify square matrix. Accordingly, we can write $$[C]_{N\times N}^T = \begin{bmatrix} c_0 & c_3 & 0 & 0 & 0 & 0 & \ldots & \ldots & c_2 & c_1 \\ c_1 & -c_2 & 0 & 0 & 0 & 0 & \ldots & \ldots & c_3 & -c_0 \\ c_2 & c_1 & c_0 & c_3 & 0 & 0 & 0 & \ldots & 0 & 0 \\ c_3 & -c_0 & c_1 & -c_2 & 0 & 0 & 0 & \ldots & 0 & 0 \\ \vdots & \vdots & \vdots & \vdots & \vdots & \vdots & \vdots & \vdots & \vdots & \vdots \\ \vdots & \vdots & \vdots & \vdots & \vdots & \vdots & \vdots & \vdots & \vdots & \vdots \\ 0 & 0 & 0 & 0 & \ldots & 0 & c_0 & c_3 & 0 & 0 \\ 0 & 0 & 0 & 0 & \ldots & 0 & c_1 & -c_2 & 0 & 0 \\ 0 & 0 & 0 & 0 & \ldots & 0 & c_2 & c_1 & c_0 & c_3 \\ 0 & 0 & 0 & 0 & \ldots & 0 & c_3 & -c_0 & c_1 & -c_2 \end{bmatrix}_{N\times N}. \qquad (7)$$

In what follows, we consider the D4 Daubechies wavelets and extend the input data by using a simple convolution. Accordingly, the approximate coefficients at scale m=1 contained in $\hat{W}^{(1)}$ after threshold can be determined by the following matrix equation.

$$\begin{Bmatrix} \hat{s}_{1,0} \\ \hat{s}_{1,1} \\ \hat{s}_{1,2} \\ \hat{s}_{1,3} \\ \vdots \\ \vdots \\ \vdots \\ \hat{s}_{1,(\frac{N}{2}-2)} \\ \hat{s}_{1,(\frac{N}{2}-1)} \end{Bmatrix}_{\frac{N}{2}\times 1} = \frac{1}{\sqrt{2}} \begin{bmatrix} c_0 & c_3 & 0 & 0 & 0 & \ldots & \ldots & c_2 & c_1 \\ c_1 & -c_2 & 0 & 0 & 0 & \ldots & \ldots & c_3 & -c_0 \\ c_2 & c_1 & c_0 & c_3 & 0 & \ldots & \ldots & 0 & 0 \\ c_3 & -c_0 & c_1 & -c_2 & 0 & \ldots & \ldots & 0 & 0 \\ 0 & 0 & c_2 & c_1 & c_0 & c_3 & \ldots & \ldots & 0 & 0 \\ 0 & 0 & c_3 & -c_0 & c_1 & -c_2 & \ldots & \ldots & 0 & 0 \\ 0 & 0 & 0 & 0 & 0 & 0 & \ddots & \ldots & \vdots & \vdots \\ \vdots & \vdots & \vdots & \vdots & \vdots & \vdots & \ldots & \ddots & \vdots & \vdots \\ 0 & 0 & 0 & 0 & 0 & 0 & \ldots & \ldots & c_0 & c_3 \\ 0 & 0 & 0 & 0 & 0 & 0 & \ldots & \ldots & c_1 & -c_2 \end{bmatrix}_{\frac{N}{2}\times \frac{N}{2}} \qquad (8)$$

-continued $$\begin{Bmatrix} \hat{S}_{2,0} \\ \hat{T}_{2,0} \\ \hat{S}_{2,1} \\ \hat{T}_{2,1} \\ \vdots \\ \vdots \\ \vdots \\ \hat{S}_{2,(\frac{N}{4}-1)} \\ \hat{T}_{2,(\frac{N}{4}-1)} \end{Bmatrix}_{\frac{N}{2} \times 1}.$$

Note that $(\hat{T}_{2,0}, \hat{T}_{2,1}, \hat{T}_{2,2}, \ldots, \hat{T}_{2,(N/4-1)})$ on the right side of Eq. (8) contain the wavelet coefficients at scale m=2 after threshold, which are known. The approximation coefficients $(\hat{S}_{2,0}, \hat{S}_{2,1}, \hat{S}_{2,2}, \ldots, \hat{S}_{2,(N/4-1)})$ are to be determined by the following matrix equation.

$$\begin{Bmatrix} \hat{S}_{2,0} \\ \hat{S}_{2,1} \\ \hat{S}_{2,2} \\ \hat{S}_{2,3} \\ \vdots \\ \vdots \\ \vdots \\ \hat{S}_{2,(\frac{N}{4}-2)} \\ \hat{S}_{2,(\frac{N}{4}-1)} \end{Bmatrix}_{\frac{N}{4} \times 1} = \frac{1}{\sqrt{2}} \begin{bmatrix} c_0 & c_3 & 0 & 0 & 0 & 0 & \cdots & \cdots & c_2 & c_1 \\ c_1 & -c_2 & 0 & 0 & 0 & 0 & \cdots & \cdots & c_3 & -c_0 \\ c_2 & c_1 & c_0 & c_3 & 0 & 0 & \cdots & \cdots & 0 & 0 \\ c_3 & -c_0 & c_1 & -c_2 & 0 & 0 & \cdots & \cdots & 0 & 0 \\ 0 & 0 & c_2 & c_1 & c_0 & c_3 & \cdots & \cdots & 0 & 0 \\ 0 & 0 & c_3 & -c_0 & c_1 & -c_2 & \cdots & \cdots & 0 & 0 \\ 0 & 0 & 0 & 0 & c_2 & c_1 & \ddots & \cdots & \vdots & \vdots \\ \vdots & \vdots & \vdots & \vdots & \vdots & \vdots & \cdots & \ddots & \vdots & \vdots \\ 0 & 0 & 0 & 0 & 0 & 0 & \cdots & \cdots & c_0 & c_3 \\ 0 & 0 & 0 & 0 & 0 & 0 & \cdots & \cdots & c_1 & -c_2 \end{bmatrix}_{\frac{N}{4} \times \frac{N}{4}} \quad (9)$$

$$\begin{Bmatrix} \hat{S}_{3,0} \\ \hat{T}_{3,0} \\ \hat{S}_{3,1} \\ \hat{T}_{3,1} \\ \vdots \\ \vdots \\ \vdots \\ \hat{S}_{3,(\frac{N}{8}-1)} \\ \hat{T}_{3,(\frac{N}{8}-1)} \end{Bmatrix}_{\frac{N}{4} \times 1}$$

Once again, the elements $(\hat{T}_{3,0}, \hat{T}_{3,1}, \hat{T}_{3,2}, \ldots, \hat{T}_{3,(N/8-1)})$ on the right side of Eq. (9) represent the wavelet coefficients at scale m=3 after threshold, which are specified, but $(\hat{S}_{3,0}, \hat{S}_{3,1}, \hat{S}_{3,2}, \ldots, \hat{S}_{3,(N/8-1)})$ are to be determined by the matrix equation involving wavelet and approximation coefficients at the next scale after threshold. At scale m=M−2, we can solve $(\hat{S}_{(M-2),0}, \hat{S}_{(M-2),1}, \hat{S}_{(M-2),2}, \hat{S}_{(M-2),3})$ in terms of $(\hat{T}_{(M-1),0}, \hat{T}_{(M-1),1})$ and $(\hat{S}_{(M-1),0}, \hat{S}_{(M-1),1})$ at scale m=M−1 after threshold as $$\begin{Bmatrix} \hat{S}_{(M-2),0} \\ \hat{S}_{(M-2),1} \\ \hat{S}_{(M-2),2} \\ \hat{S}_{(M-2),3} \end{Bmatrix}_{4 \times 1} = \frac{1}{\sqrt{2}} \begin{bmatrix} c_0 & c_3 & c_2 & c_1 \\ c_1 & -c_2 & c_3 & -c_0 \\ c_2 & c_1 & c_0 & c_3 \\ c_3 & -c_0 & c_1 & -c_2 \end{bmatrix}_{4 \times 4} \begin{Bmatrix} \hat{S}_{(M-1),0} \\ \hat{T}_{(M-1),0} \\ \hat{S}_{(M-1),1} \\ \hat{T}_{(M-1),1} \end{Bmatrix}_{4 \times 1}, \quad (10)$$

where $(\hat{S}_{(M-1),0}, \hat{S}_{(M-1),1})$ on the right side of Eq. (10) are given by $$\begin{Bmatrix} \hat{S}_{(M-1),0} \\ \hat{S}_{(M-1),1} \end{Bmatrix}_{2 \times 1} = \frac{1}{\sqrt{2}} \begin{bmatrix} c_0 + c_2 & c_1 + c_3 \\ c_1 + c_3 & -c_0 - c_2 \end{bmatrix}_{2 \times 2} \begin{Bmatrix} \hat{S}_{M,0} \\ \hat{T}_{M,0} \end{Bmatrix}_{2 \times 1}, \quad (11)$$

where $(\hat{S}_{M,0}, \hat{T}_{M,0})$ on the right side of Eq. (11) are the approximation and wavelet coefficients at scale m=M after threshold, respectively, which are known. Substituting these quantities into the wavelet vector at scale m=1 after threshold, we obtain:

$$\hat{W}^{(1)} = (\hat{S}_{1,0}, \hat{T}_{1,0}, \hat{S}_{1,1}, \hat{T}_{1,1}, \hat{S}_{1,2}, \hat{T}_{1,2}, \ldots, \hat{S}_{1,(N/2-1)}, \hat{T}_{1,(N/2-1)}). \quad (12)$$

The coherent structure of the input data can now be extracted by Eq. (1). It is important to understand that in general the noise embedded in the input data cannot be completely eliminated, and the extracted parts may be imperfect. This is because no prior knowledge about the test environment and conditions, and background noise are available. Suppression of noise in the input data is accomplished through threshold, which either sets the wavelet coefficients to zero or leave them as they are. Also, threshold tends to reduce the amplitudes of the extracted information. These will affect the quality of the extracted information. Thus, the more information about the target signal can be incorporated in the process, the higher the quality of the extracted information becomes.

Equation (1) enables us to suppress noise imbedded in the input data. However, there can be useful information in these sanitized data at each individual scale. Detailed formulations for extracting this useful information are derived at each scale. These are described as follows.

Suppose that we want to extract specific information at scale m from the sanitized data given by Eq. (1). Note that each scale describes a different frequency band. The higher the scale value m is, the higher the frequency band is. The formulations for extracting specific information from each scale m can be expressed as $$\{x^{(m)}\}_{N\times 1} = 2^{-1/2}[C]_{N\times N}^T\{W^{(m)}\}_{N\times 1}, \quad (13)$$

where m=1, 2, . . . , M-1. The wavelet vector $W^{(m)}$ is specified with all wavelet coefficients set to zero, except those at the scale m.

For example, to extract target information at scale m=1, we can start from the fully decomposed wavelet vector after threshold $$W^M = (\hat{S}_{M,0}, \hat{T}_{M,0}, \hat{T}_{(M-1),0}, \hat{T}_{(M-1),1}, \ldots, \hat{T}_{2,0}, \hat{T}_{2,1}, \hat{T}_{2,2}, \ldots, \hat{T}_{2,(N/4-1)}, \hat{T}_{1,0}, \hat{T}_{1,1}, \hat{T}_{1,2}, \ldots, \hat{T}_{1,(N/2-1)}). \quad (14)$$

Next, we set all coefficients set to zero, except the wavelet coefficients at the scale m=1.

$$W^{(M)} = (0, 0, \ldots, \hat{T}_{1,0}, \hat{T}_{1,1}, \hat{T}_{1,2}, \ldots, \hat{T}_{1,(N/2-1)}). \quad (15)$$

The approximation coefficients from scales m=M-1 down to m=1 can be determined by, $$\hat{S}_{m-1,n} = \frac{1}{\sqrt{2}} \sum_{k=0}^{N_k-1} \left(c_{n-2k}\hat{S}_{m,k} + b_{n-2k}\hat{T}_{m,k}\right), \quad (16)$$

where $b_k = (-1)^k c_{3-k}$, and the sum of all the coefficients $b_k$ is zero. Once the approximation coefficients are specified, the wavelet vector at scale m=1 is established. Using the universal threshold (3), we can write $$W^{(1)} = (\tilde{S}_{1,0}, \tilde{T}_{1,0}, \tilde{S}_{1,1}, \tilde{T}_{1,1}, \ldots, \tilde{S}_{1,(N/2-1)}, \tilde{T}_{1,(M/2-1)}). \quad (17)$$

The extracted information at scale m=1 can then be written as $$\{x^{(1)}\}_{N\times 1} = 2^{-1/2}[C]_{N\times N}^T\{W^{(1)}\}_{N\times 1}. \quad (18)$$

In a similar manner, we can extract information at scale m by setting all other coefficients of the fully decomposed wavelet vector to zero after threshold, except the wavelet coefficients at the scale m.

$$W^{(M)} = (0, 0, \ldots, \hat{T}_{m,0}, \hat{T}_{m,1}, \hat{T}_{m,2}, \ldots, 0, 0, \ldots) \quad (19)$$

Using Eq. (16) and the universal threshold (3), we can determine the wavelet vector at scale m as $$W^{(m)} = (\tilde{S}_{1,0}, \tilde{T}_{1,0}, \tilde{S}_{1,1}, \tilde{T}_{1,1}, \ldots, \tilde{S}_{1,(N/2-1)}, \tilde{T}_{1,(N/2-1)}). \quad (20)$$

Substitute $W^{(m)}$ into Eq. (13) leads to the extracted information at scale m.

To summarize, the new process enables one to sanitize the directly measured data and extract specific information at any scale m by using, say, the D4 Daubechies wavelets. These are depicted by Eqs. (13) to (20). Detailed steps involved in these procedures are as follows:

1. Extend any set of measured data $\{x\}_{N\times 1}$ using a simple convolution, where $N=2^M$.
2. Set the approximation coefficients $S_{0,i} = x_{0,i}$, here $x_{0,i}$ are the given set of input data with i=0, 1, 2, . . . , N.
3. Calculate the scaling and wavelet coefficients $S_{m,n}$ and $T_{m,n}$ using the following equations $$S_{m+1,n} = \frac{1}{\sqrt{2}} \sum_{k=0}^{N_k-1} c_k S_{m,2n+k} \text{ or } S_{m+1,n} = \frac{1}{\sqrt{2}} \sum_{k=0}^{N_k-1} c_{k-2n} S_{m,k} \quad (21)$$

$$T_{m+1,n} = \frac{1}{\sqrt{2}} \sum_{k=0}^{N_k-1} b_k S_{m,2n+k} \text{ or } T_{m+1,n} = \frac{1}{\sqrt{2}} \sum_{k=0}^{N_k-1} b_{k-2n} S_{m,k} \quad (22)$$

4. Once the approximation and wavelet coefficients at all scales are determined, the signal is said to be fully decomposed.

$$W^{(M)} = (S_{M,0}, T_{M,0}, T_{(M-1),0}, T_{(M-1),1}, \ldots, T_{2,0}, T_{2,1}, \ldots, T_{2,(N/4-1)}, T_{1,0}, T_{1,1}, T_{1,2}, \ldots, T_{1,(N/2-1)}). \quad (23)$$

5. Apply the universal threshold $\lambda_U$ to $W^{(M)}$ at scale m=M $$W_i^{(M)} = \begin{cases} 0 & |W_i| < \lambda_U \\ W_i & |W_i| \geq \lambda_U \end{cases}, \quad (24)$$

where the threshold is given by $$\lambda_U = \sqrt{2\ln N}\hat{\sigma}, \quad (25)$$

where $(2 \ln N)^{1/2}$ is the expected maximum value of the white noise sequence with length N and $\hat{\sigma}$ is a robust estimate of the standard deviation of the noise in the signal under consideration. Typically $\hat{\sigma}$ is taken at the median of absolute deviation (MAD) of the wavelet coefficients at the smallest scale m=1 divided by 0.6745 to calibrate with the standard deviation of Gaussian distribution, where $\hat{\sigma} = 0.6745 \times \text{median}[|T_{1,i} - \text{median}(T_{1,i})|]$.

6. Use the universal threshold to determine the wavelet coefficients at all scales.

$$(\hat{T}_{M,0}, \hat{T}_{(M-1),0}, \hat{T}_{(M-1),1}, \ldots, \hat{T}_{2,0}, \hat{T}_{2,1}, \hat{T}_{2,2}, \ldots, \hat{T}_{2,(N/4-1)}, \hat{T}_{1,0}, \hat{T}_{1,1}, \hat{T}_{1,2}, \ldots, \hat{T}_{1,(N/2-1)}). \quad (26)$$

7. Use the following equation to specify the approximation coefficients from scales m=M-1 to m=1 after threshold $(\hat{S}_{m,0}, \hat{S}_{m,1}, \hat{S}_{1,2}, \ldots, \hat{S}_{m(N/2^m-2)}, S_{1,(N/2^m-1)})$.

$$\hat{S}_{m-1,n} = \frac{1}{\sqrt{2}} \sum_{k=0}^{3} \left(c_{n-2k}\hat{S}_{m,k} + b_{n-2k}\hat{T}_{m,k}\right). \quad (27)$$

8. Determine the wavelet vector at the scale m=1 after threshold using the following equation.

$$\hat{W}^{(1)} = (\hat{S}_{1,0}, \hat{T}_{1,0}, \hat{S}_{1,1}, \hat{T}_{1,1}, \hat{S}_{1,2}, \hat{T}_{1,2}, \ldots, \hat{S}_{1,(N/2-1)}, \hat{T}_{1,(N/2-1)}). \quad (28)$$

9. Use Eq. (4) to set up the square matrix for the scaling coefficients $[C]_{N\times N}$, and Eq. (7) to find its inversion.

10. The original mixture of data can now be sanitized by using the following equation $$\{x\}_{N\times 1} = 2^{-1/2}[C]_{N\times N}^T\{\hat{W}^{(1)}\}_{N\times 1}, \quad (29)$$

11. To extract specific information at any scale m, we set all wavelet coefficients to zero in the fully decomposed wavelet vector after threshold, except those at the scale m.

$$W^{(m)} = (0, 0, \ldots, \hat{T}_{m,0}, \hat{T}_{m,1}, \hat{T}_{m,2}, \ldots, 0, 0, \ldots). \quad (30)$$

12. Use Eq. (27) to determine the approximation coefficients from scales m=M-1 to m=1.

13. Establish the wavelet vector at scale m and apply the universal threshold (3) to get, $$W^{(m)} = (\tilde{S}_{1,0}, \tilde{T}_{1,0}, \tilde{S}_{1,1}, \tilde{T}_{1,1}, \ldots, \tilde{S}_{1,(N/2-1)}, \tilde{T}_{1,(N/2-1)}). \quad (32)$$

14. The extracted information at scale m can now be written as $$\{x^{(m)}\}_{N\times 1} = 2^{-1/2} [C]_{N\times N}^T \{W^{(m)}\}_{N\times 1}. \quad (33)$$

Extraction of specific information can be very effective when some prior knowledge is incorporated in the process. For example, suppose that information over a specific frequency band is desired. Then we can focus on the scale that corresponds to this frequency band and extract the target information. If no information regarding the target information is available, it becomes a completely blind extraction. Under this condition, one can still use the steps outlined above to extract coherent structures from the measured data or simply sanitize the input data.

Figure 3:
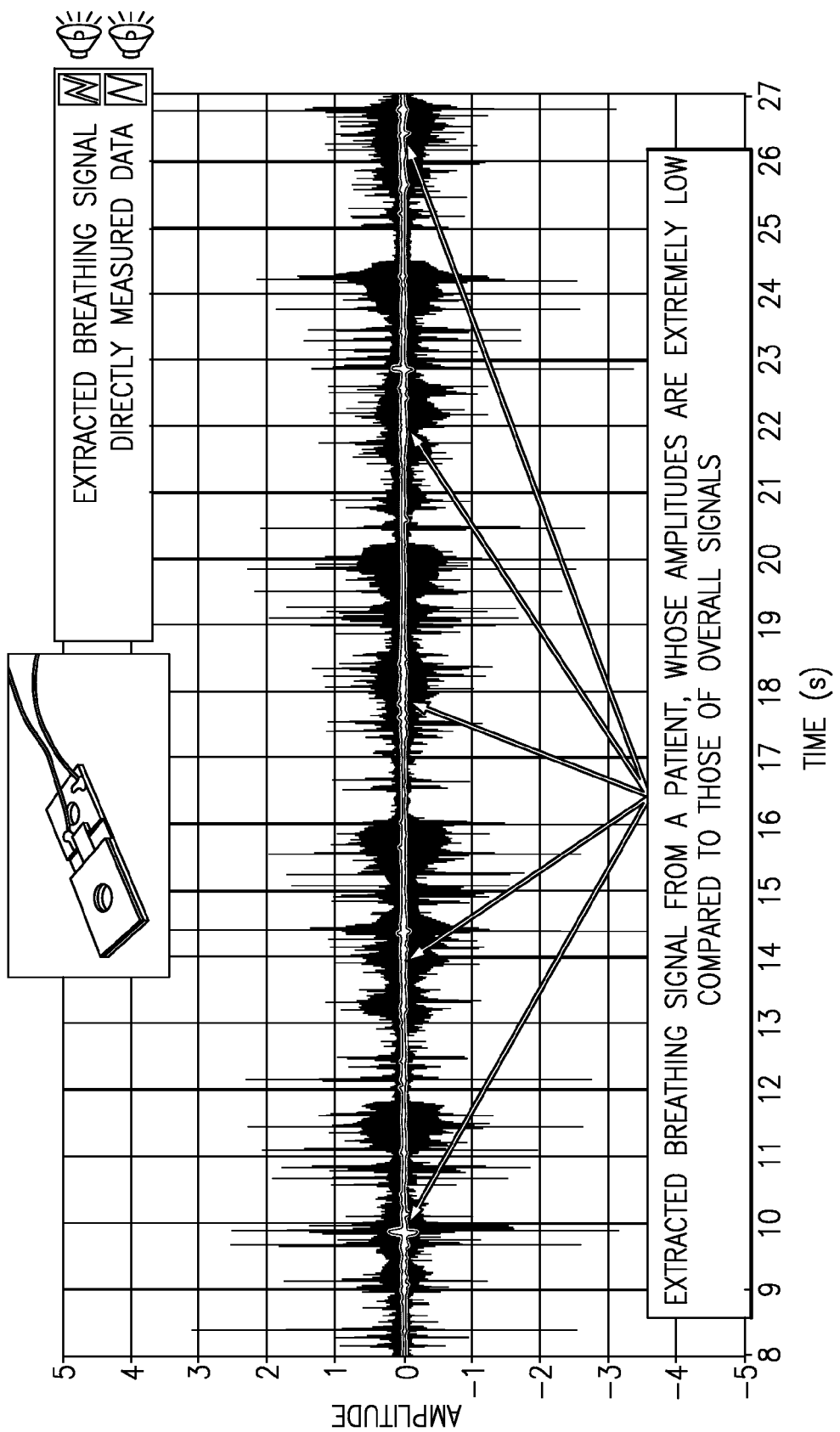
FIG. 3 is a comparison of the extracted breathing signal of a patient versus the directly measured data. Extraction was done using Eq. (33) without any prior knowledge of the characteristics of both target features and interfering and background noise whatsoever, where and how signals are collected.

FIG. 3 illustrates an example of a complete blind extraction of coherent structures of mixed signals without any prior knowledge of how and where signals are measured, and what the characteristics of target information, and interfering signals and random background noise are.

These data were collected by a sensor taped on an asthma patient to detect early signs asthma attack. The black line in FIG. 3 represents the overall measured data and the white line is the extracted signal. Since the amplitudes of breathing signals are so low compared to those of overall signals, they are completely masked by the interfering signals and random background noise, including the doctor's voice. If the recorded signals are played back, there is no way of noticing the patient's breathing, which makes it impossible to monitor an early asthma attack. However, by following the steps 1 to 14 as outlined above, we are able to sanitize the data and extract patient's breathing signal. In other words, all interfering signals and random background noise including doctor's voice are successfully suppressed.

In accordance with the provisions of the patent statutes and jurisprudence, exemplary configurations described above are considered to represent a preferred embodiment of the invention. However, it should be noted that the invention can be practiced other than as specifically illustrated and described without departing from its spirit or scope.

What is claimed is:

1. A method for extracting a target signal from measured signal including the steps of:
    a) measuring a target signal and background noise to obtain measurement data;
    b) using a computer to extract coherent structure from the measurement data using wavelets and corresponding wavelet coefficients;
    c) comparing the wavelet coefficients of the wavelets with a threshold with the computer;
    d) eliminating the wavelet coefficients of the wavelets that are less than the threshold with the computer;
    e) determining approximation coefficients at a selected scale m after said steps a)-d) based upon the wavelet coefficients at scale m;
    f) determining a wavelet vector at scale m based upon the approximation coefficients; and
    g) extracting information at scale m based upon the wavelet vector with all wavelet coefficients set to zero except those at the scale m.

2. The method of claim 1 wherein the step of extracting includes setting all wavelet coefficients of the wavelet vector to zero except those at scale m.

3. The method of claim 2 wherein the at least one sensor includes a microphone and the target signal is a person's voice.

4. The method of claim 2 wherein the target signal is sound.

5. The method of claim 2 wherein the target signal is a patient's breathing.

6. A system for extracting a target signal from measured signal including:
    at least one sensor for measuring a target signal and background noise to obtain measurement data;
    a computer programmed to extract coherent structure from the measurement data using wavelets and corresponding wavelet coefficients; and
    the computer further programmed to compare the wavelet coefficients of the wavelets with a threshold and eliminate the wavelet coefficients of the wavelets that are less than the threshold, the computer programmed to determine approximation coefficients at a selected scale m based upon the wavelet coefficients at scale m, the computer programmed to determine a wavelet vector at scale m based upon the approximation coefficients, wherein the computer is further programmed to extract information at scale m based upon the wavelet vector with all wavelet coefficients set to zero except those at the scale m.

7. The system of claim 6 wherein the computer is further programmed set all wavelet coefficients of the wavelet vector to zero except those at scale m.

8. The system of claim 7 wherein the at least one sensor includes a microphone and the target signal is a person's voice.

9. The system claim 7 wherein the at least one sensor includes a microphone and the target signal is sound.

10. The system of claim 7 wherein the target signal is a patient's breathing.

* * * * *